United States Patent [19]

Doubleday

[11] Patent Number: 5,470,306
[45] Date of Patent: Nov. 28, 1995

[54] MEDICAL BANDAGING ARTICLE AND PACKAGING SYSTEM

[75] Inventor: Walter D. Doubleday, Jupiter, Fla.

[73] Assignee: Kirschner Medical Corporation, Timonium, Md.

[21] Appl. No.: 200,405

[22] Filed: Feb. 23, 1994

[51] Int. Cl.⁶ ........................................................ A61F 5/00
[52] U.S. Cl. ................................. 602/8; 602/6; 602/41; 602/44; 206/390
[58] Field of Search ..................................... 602/1, 5, 6, 7, 602/8, 41, 49, 47, 60, 61; 206/390, 440, 441, 820; 229/237

[56] References Cited

U.S. PATENT DOCUMENTS

| | | |
|---|---|---|
| 3,421,501 | 1/1969 | Beightol . |
| 3,557,156 | 1/1971 | Enneper et al. . |
| 3,630,194 | 12/1971 | Boardman . |
| 3,645,925 | 2/1972 | Speranza et al. . |
| 3,686,725 | 8/1972 | Nisbet et al. . |
| 3,787,272 | 1/1974 | Nisbet et al. . |
| 3,881,473 | 5/1975 | Corvi et al. . |
| 3,882,857 | 5/1975 | Woodall, Jr. . |
| 3,900,024 | 8/1975 | Lauber et al. . |
| 3,923,049 | 12/1975 | Lauber et al. . |
| 4,052,282 | 10/1977 | Kubushiro . |
| 4,105,025 | 8/1978 | Wang et al. . |
| 4,131,114 | 12/1978 | Kirkpatrick et al. . |
| 4,134,397 | 1/1979 | Gianakakos et al. . |
| 4,235,228 | 11/1980 | Gaylord, Jr. et al. . |
| 4,306,549 | 12/1981 | Canie . |
| 4,306,656 | 12/1981 | Dahlem .................................. 206/390 |
| 4,344,423 | 8/1982 | Evans et al. . |
| 4,376,438 | 3/1983 | Straube et al. . |
| 4,411,262 | 10/1983 | von Bonin et al. . |
| 4,433,680 | 2/1984 | Yoon . |
| 4,442,833 | 4/1984 | Dahlen et al. . |
| 4,502,479 | 3/1985 | Garwood et al. . |
| 4,570,622 | 2/1986 | von Bonin et al. . |
| 4,598,528 | 7/1986 | McFarland et al. . |
| 4,609,578 | 9/1986 | Reed . |
| 4,628,917 | 12/1986 | Campagna, Jr. et al. . |
| 4,667,661 | 5/1987 | Scholz et al. . |
| 4,676,861 | 6/1987 | Bishop . |
| 4,705,840 | 11/1987 | Buckanin . |
| 4,770,299 | 9/1988 | Parker . |
| 4,774,937 | 10/1988 | Scholz et al. . |
| 4,869,046 | 9/1989 | Parker . |
| 4,899,738 | 2/1990 | Parker . |
| 5,016,622 | 5/1991 | Norvell . |
| 5,027,803 | 7/1991 | Scholz et al. . |
| 5,171,208 | 12/1992 | Edenbaum et al. . |

Primary Examiner—Linda C. Dvorak
Attorney, Agent, or Firm—Banner & Allegretti, Ltd.

[57] ABSTRACT

A medical bandaging article sealed in moisture-free condition, serially connected with other such sealed articles in roll form. The medical bandaging article comprises an open cell foam layer and a woven fabric layer with several layers of resin impregnated substrates arranged therebetween. The substrate layers are preferably smaller than the fabric and foam layers. A heat fusing web is interposed between the fabric layer and the immediately adjacent substrate layer, and extends beyond the substrates so that upon application of sufficient heat and pressure, the fabric layer and the foam layer are fused together around the periphery of the substrates encasing them between the fabric layer and foam layer. A roll of individually sealed pouches containing bandaging articles are connected together, and between adjoining sealed pouches special perforations are provided for separating the pouches without damaging the seals of the adjacent pouches.

14 Claims, 3 Drawing Sheets

MEDICAL BANDAGING ARTICLE AND PACKAGING SYSTEM

BACKGROUND OF THE INVENTION

The present invention relates generally to the field of orthopedic bandaging articles, such as casts and splints, for immobilizing body parts, and more specifically to an improved construction for a moisture-curable resin bandaging article and packaging system therefor.

Orthopedic bandages used in the treatment of injuries requiring immobilization of a body member are generally formed from a strip of fabric or scrim material impregnated with a substance which hardens after the strip has been wrapped around or used to support the body member. Traditionally plaster-of-Paris has been used as the hardening substance.

Typically plaster-of-Paris has been used to construct a cast or splint for an injured body member by first applying a protective covering layer of cotton fabric or the like to the body member and then applying the fabric impregnated with plaster-of-Paris which has been wetted in water immediately before application. Plaster-of-Paris is generally considered easy to work but also has numerous disadvantages. For example, several layers of the impregnated and wetted fabric must be applied to obtain a sufficient strong cast or splint, and plaster-of-Paris has a relatively low strength to weight ratio which results in a heavy and bulky bandage. Plaster-of-Paris bandages are also slow to harden, sometimes requiring a few days to reach maximum strength. Also, plaster-of-Paris breaks down in water which limits or prohibits some activities of a patient, such as bathing.

A significant advance in the art of hardenable bandaging has been made in the development of moisture-curable resins which are impregnated or coated onto fabrics which are maintained in moisture-free conditions until use. Another development in this art has been the use of fiberglass fabrics or substrates onto which the resin is impregnated or coated. U.S. Pat. No. 4,411,262 to von Bonin et al. discloses a constructional material which is stable in moisture-free storage conditions, but which hardens upon exposure to moisture, either by direct wetting or by the moisture in the air. U.S. Pat. No. 4,433,680 to Yoon discloses a prepolymer which is used with moisture-curable resin to give the bandage increased shelf stability and improved set time.

Compared to plaster-of-Paris, curable resin products are lightweight, have a relatively high strength to weight ratio and can be made relatively porous. Prior art moisture-curing bandages include layers of resin impregnated substrates arranged between layers of closed cell foam, open cell foam, various fabrics and sometimes enveloped in tubular fabrics or stockinets. If the several layers of substrates, fabrics, foams, etc. are not held together, once wetted, they can move relative to one another and result in messy application or improper positioning of the layers to harden in the most effective manner. In addition, since most bandaging products have a side which is specifically suited for application to the skin of the patient while the other side is specifically suited to be the outer side, when the substrates, foams, etc. are enveloped in stockinets, it is difficult for the doctor or technician to determine which side should be applied to the skin.

The prior art bandages have typically been individually packaged in pouches made of metal foil and plastic film laminated together. U.S. Pat. Nos. 4,770,299, 4,869,046 and 4,899,738 to Parker disclose moisture-curable bandaging products in a convenient roll form in which the packaging is tubular and coextensive with the bandaging product. A desired length of bandaging product is removed from the package by cutting through the package and bandaging product and then resealing the roll. A disadvantage of this configuration is that once the sealed package is cut, air enters the roll package and when the package is resealed the atmospheric moisture from the air causes some of the bandaging product, particularly near the seal, to harden. Subsequent use of the bandaging product requires that the hardened areas be discarded resulting in waste which is a significant economical drawback since the effective cost of the product is increased. Another disadvantage of the coextensive package and bandaging product configuration is the difficulty in cutting two layers of the strong foil-plastic film packaging material, top and bottom, as well as several layers of fiberglass substrate, and any intervening fabric layers or resin. Tied to this problem is the need to clean the cutting tools, such as scissors, used to cut the package/bandaging product since they can easily become coated with resin.

The moisture-curable resin bandaging products discussed above still possess disadvantages which complicate their use and increase the effective cost of the products.

SUMMARY OF THE INVENTION

It is therefore an object of the present invention to provide a unitary bandaging article with a substrate impregnated with moisture-curable resin which hardens upon exposure to moisture to form a lightweight and rigid structure.

It is anther object of the invention to provide a cushioning layer next to the skin of the patient for maximum comfort and protection.

Another object of the invention is to provide a unitary bandaging article having easily identifiable skin and outer sides to facilitate application to the injured body member.

Still another object of the invention is to provide a unitary bandaging article which provides for proper positioning of the substrate, foam and fabric layers to ensure clean, easy application and proper hardening.

Yet another object of the invention is to provide a packaging system for containing bandaging articles in moisture-impervious individually sealed pouches connected together in a convenient roll form to facilitate dispensing.

Directed to achieving these objects, the preferred embodiment of the invention disclosed below provides a medical bandaging article sealed in a moisture-free condition, serially connected with other such sealed articles in roll form. The medical bandaging article comprises an open cell foam layer and a woven fabric layer with several layers of resin impregnated substrates arranged therebetween. In the preferred embodiment of the invention, the substrates are smaller than the foam and fabric layers, and a single piece of heat fusing web material which is larger than the substrate layer is interposed between the fabric layer and the immediately adjacent substrate. In this manner, the heat fusing web both overlays and extends beyond the periphery of the substrates so that upon application of sufficient heat and pressure, the fabric layer and the foam layer are fused together around the periphery of the substrates thereby encasing the several layers of substrates. This ensures that the fabric, foam and substrate layers are maintained in proper position during hardening. Since the heat fusing web overlays the substrates, it also forms a barrier which prevents seepage of resin through the fabric.

Alternative embodiments of the invention include positioning strips of heat fusing web material around the substrates such that the foam layer and fabric layer will be fused together to encase the substrates therebetween. Another possibility is the use of a single piece of heat fusing web material having a central opening which coincides with the size and shape of the substrates so that the fusing web material is disposed around the periphery of the substrates but does not overlay them. The foam and fabric layers are fused together to encase the substrates, but no barrier is formed. Obviously, these two embodiments would be suitable for articles made with seepage-proof fabric layers. Still another possibility is to fuse only one seam of the article and attach the other seams by other fastening means, such as stitching.

A roll of individually sealed pouches containing bandaging articles are connected together for easy dispensing of the articles. Between adjoining sealed pouches special perforations are provided for separating the pouches without damaging the seals of the adjacent pouches.

These and other features and advantages of the invention may be more completely understood from the following detailed description of the preferred embodiment of the invention with reference to the accompanying drawings.

DETAILED DESCRIPTION OF THE PREFERRED EMBODIMENTS

Figure 1:
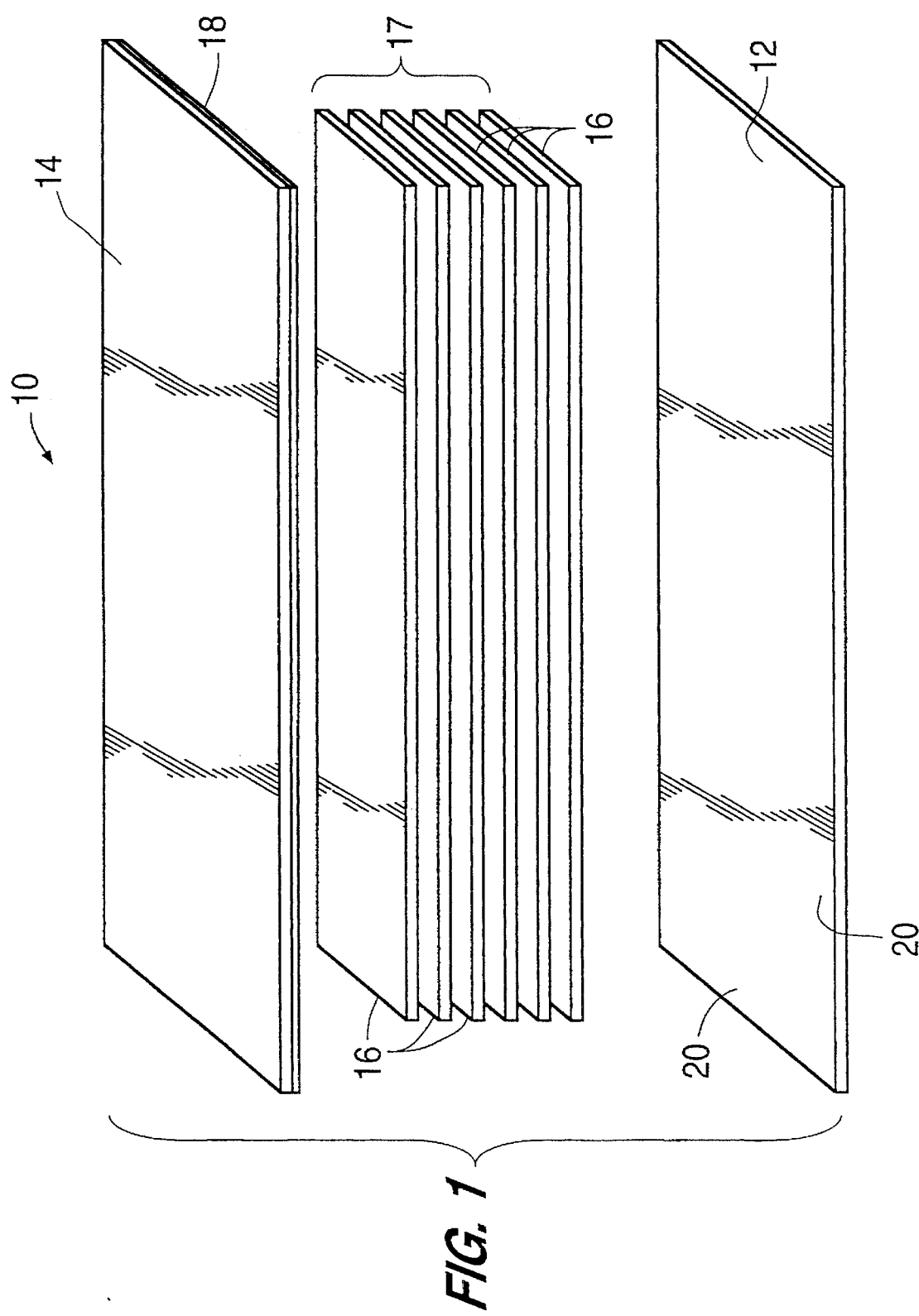
FIG. 1 is a perspective, schematic exploded view of the medical bandaging article in accordance with the present invention.

Referring to FIG. 1, an exploded view of bandaging article 10 includes an open cell foam layer 12 which is applied against the skin of the patient and provides a cushioning layer for comfort and protection. Foam layer 12 is preferably one-fourth inch thick. Commonly available open cell foam such as polyurethane is used for foam layer 12 since open cell foams are water and air permeable and inexpensive. Open cell foams aid in wetting the article during application. A soft, woven fabric layer 14 forms the opposite side of article 10 which will preferably be the outer side when applied to the patient. Since foam and fabric have readily distinguishable textures, a doctor or technician can easily place the article with the foam layer against the skin of the patient without delay and guesswork. A plurality of substrate layers 16 are arranged between foam layer 12 and fabric layer 14.

As shown in FIG. 1, the preferred embodiment of the present invention comprises between six and eight substrate layers 16 in vertical alignment such that they overlay one another. The substrate layers collectively may be referred to as a substrate 17 for convenience. Each substrate layer is preferably knit of fiberglass fibers having a mesh size of approximately 240 openings per square inch. The preferred mesh size has been determined to provide an advantageous balance between surface area for impregnating or coating with resin, and porosity. The higher the mesh size, the larger the amount of surface area which can be impregnated or coated with resin which results in higher strength of the bandaging article. However, too high a mesh size presents the disadvantage of limiting the porosity of the substrate. For the construction of the present invention, six to eight substrate layers of 240 mesh size is preferred. It will be understood that "mesh size" as herein used is determined as a function of the courses and wales of the knit fiberglass fabric which bound the openings.

Substrate layers 16 are impregnated or coated with moisture-curable resin which is storage stable when maintained in moisture-free conditions, but hardens upon exposure to sufficient moisture to form a rigid, lightweight and strong protective structure. Substrate layers 16 are preferably untreated in any way prior to impregnation or coating on of the resin. The formulation of the reaction system of the moisture-curable resin is known, and a complete discussion thereof, can be found in the aforementioned U.S. Pat. No. 4,411,262.

The resin may be applied to the substrate layers in any suitable manner, such as by spraying or with rollers. A substrate layer of the present invention passes through gap rollers, one of which acts as a supply roller. The supply roller is associated with a resin reservoir, and the resin picked up by the supply roller is coated onto the substrate layer as it passes between the rollers. The amount of resin that is coated onto the substrate layer is controlled by adjusting the distance or the "gap" between the rollers.

The amount of resin used in the bandaging article of the present invention can be expressed as a percentage of the total weight of a roll of product, the roll includes the preferred number of bandaging articles, the packaging material and the core upon which the roll is wound. The core is a hollow polyethylene cylinder with a 1/16 inch flange or lip to facilitate winding. In general, the amount of resin used is monitored because of problems which occur if the substrate layers are overcoated or undercoated. Overcoating may cause excess resin to drain or move to one side of the product, particularly during shipping and storage. Obviously unevenly coated resin due to such movement is undesirable and may produce poor results when cured. Undercoating may result in poor lamination when the product is wetted and allowed to cure. An acceptable range of resin content is 41% to 46% of the total weight of a roll, with the preferred amount being 43%. These ranges and the preferred percentage can be used as quality control parameters in a manufacturing process.

Figure 2:
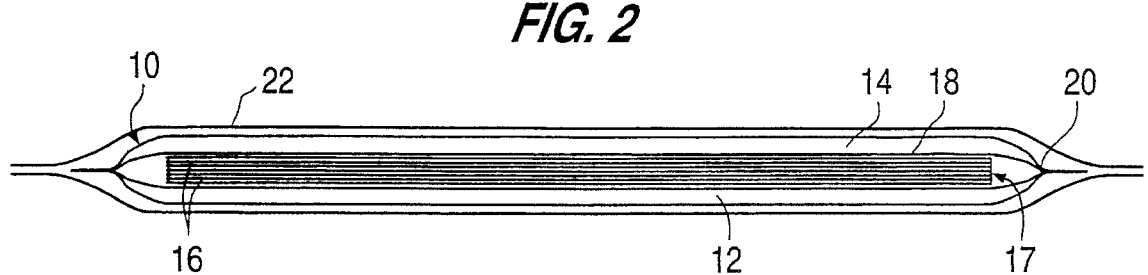
FIG. 2 is a cross-sectional view of the medical bandaging article of FIG. 1 assembled together and sealed inside a moisture-impervious pouch.

Foam layer 12 and fabric layer 14 are preferably sized larger than substrate 17 so that the foam and fabric layers can be attached together around the periphery of the substrate to encase substrate layers 16 therebetween. Encasing the substrate layers prevents them from fraying since the edges are not exposed, and furthermore maintains all of the layers in proper relation to one another to ensure optimum alignment and hardening. The preferred method for attaching foam layer 12 to fabric layer 14 around the periphery of substrate layers 16 is to provide a single heat fusing web 18 which is larger than the substrate layers, between fabric layer 14 and the immediately adjacent substrate layer. The portions of heat fusing web 18 which extend beyond the edges of substrate layers 16 preferably coincide with the fusing area 20 shown in FIG. 3. When sufficient heat and pressure is applied, the portions of fusing web 18 in fusing area 20 fuse fabric layer 14 to foam layer 12 around the periphery of substrate layers 16, encasing them therein. FIG. 2 shows a cross sectional view of the present invention, and shows substrate layers 16 encased within foam layer 12 and fabric layer 14. The heat fusing web is commercially available and widely used for fusing fabrics together in the apparel industry. A preferred fusing web is WONDERUNDER (™) and is manufactured by Pellon.

Fusing web 18 may first be fused to fabric layer 14 before assembly of article 10, as shown in FIG. 1. Once all the layers are in place, with fusing web 18 and fabric layer 14 effectively handled as a unit, then the fabric layer is fused to the foam layer in fusing area 20. Alternatively, fusing web 18 may simply be laid over substrate 17, then covered with fabric layer 14, and the fusing done as described. Regardless of the order in which fusing web 18 is introduced into the assembly, it can be seen that fusing web 18 is interposed between fabric layer 14 and the immediately adjacent substrate layer 16.

The assembly of article 10 is relatively straight forward, and varies according to how fusing web 18 is used. In general, foam layer 12 is put on an appropriate working surface, then substrate layers 16 are placed atop foam layer 12 leaving an allowance for fusing area 20. The desired number of substrate layers 16 are placed in vertical registry with one another. At this point, either (1) fabric layer 14 and fusing web 18, previously bonded together to form a unitary layer, is placed over substrate 17 and the assembly fused around the periphery of substrate 17; or (2) fusing web 18 is placed over substrate 17 with portions of web 18 extending beyond the periphery of substrate 17, and fabric layer 14 placed over fusing web 18 and the assembly fused around the periphery of substrate 17.

Although the preferred embodiment of the invention has all peripheral seams of article 10 fused together, alternative embodiments include differently shaped heat fusing webs and/or differently fastened seams. For example, strips of heat fusing web material may be positioned around the substrates such that the foam layer and fabric layer will be fused together to encase the substrates therebetween. Another example is to use a heat fusing web having outer dimensions larger than the substrates but having a central opening which coincides with the size and shape of the substrates so that the fusing web material is disposed around the periphery of the substrates but does not overlay them. The foam and fabric layers are fused together to encase the substrates, but no barrier is formed. Obviously, these embodiments would be suitable for articles made with seepage-proof fabric layers. Still another possibility is to fuse less than the entire periphery of the article and attach the remaining seams by other fastening means, such as stitching. In a rectangular article, this may mean that only one side seam is fused while the remaining three seams are otherwise fastened, or two of the side seams are fused while the remaining two seams are otherwise fastened. Of course three side seams may be fused while the remaining one seam is otherwise fastened. In all of the partially fused embodiments, the heat fusing web may be sized to overlay the substrates and the particular number of seams to be fused, or as mentioned above, strips of fusing web material may be positioned to fuse the desired seam or seams. Many combinations of fusing and otherwise fastening the seams of the bandaging article of the present invention are possible, and contemplated to be within the scope of the invention.

When foam layer 12 is fused to fabric layer 14 in accordance with the preferred embodiment, substrate layers 16 are encased therebetween and the layers of bandaging article 10 will remain in proper position for easy application. A surprising result of using a single, large heat fusing web 18 is that when bandaging article 10 is assembled with fusing web 18 overlaying substrate layers 16 and the fabric and foam layers fused around the periphery, the portion of heat fusing web 18 overlaying the substrate layers also acts as a barrier between fabric layer 14 and substrate layers 16 to prevent seepage of resin through the fabric layer. Resin seepage has posed a problem in some prior art bandaging products, especially when stored over a long period of time. Heat fusing web 18 of the present invention exhibits two functions: it fuses together the fabric and foam layers around the periphery of the substrates, and also provides a solution to the seepage problem.

Foam layer 12 attaches to the immediately adjacent substrate layer 16 during curing of the resin. Although resin seepage through the foam layer has generally not been a problem, a second, large heat fusing web, identical to heat fusing web 18, may be interposed between foam layer 12 and the immediately adjacent substrate layer so as to overlay the substrate layer, if necessary. When sufficient heat and pressure are applied, foam layer 12 and fabric layer 14 will be fused together around the periphery of substrates 16 by both heat fusing webs, and both the foam layer and fabric layer will be provided with a barrier against resin seepage.

Figure 3:
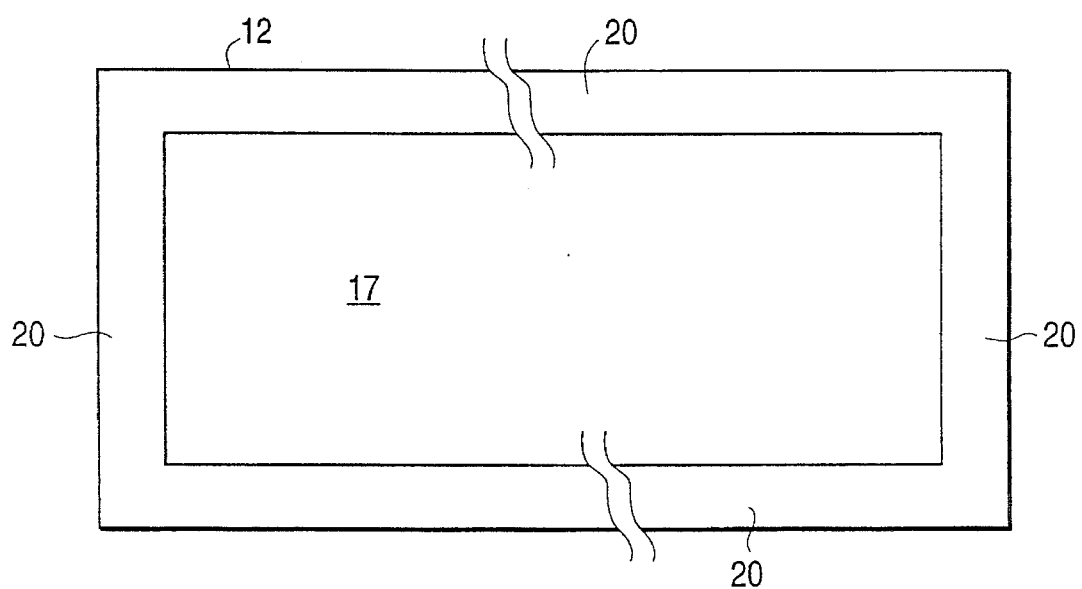
FIG. 3 is a top plan view of the open cell foam layer and a substrate layer of the medical bandaging article of FIG. 1.

Fusing area 20, which is similar to a seam allowance, is provided on both foam layer 12 and fabric layer 14. As best seen in FIG. 3, fusing area 20 is preferably of equal width around substrate layers 16 in all directions. The preferred width of fusing area 20 is one-half inch which means that substrate layers 16 are at least one-half inch smaller than the fabric and foam layers in each direction.

Figure 4:
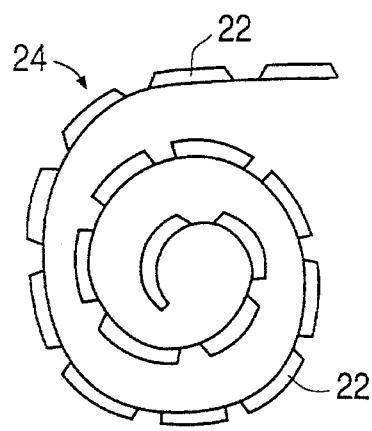
FIG. 4 is a schematic side view of the packaging system of the present invention showing a plurality of individually sealed pouches of FIG. 2 in roll

The assembled bandaging article 10 is sealed inside of moisture-impervious pouch 22 until it is ready for use, as seen in FIG. 2. The packaging system of the present invention comprises a plurality of pouches 22 connected together in a roll 24 as shown schematically in FIG. 4. Individual bandaging articles 10 are sealed separately in individual pouches 22 so that the bandaging articles can be used without the need for resealing the package. This eliminates the messy step of cutting through the packaging and substrate layers, and ensures that no air gets into a package which holds a usable product which may harden because of exposure to atmospheric moisture in the air.

Figure 5:
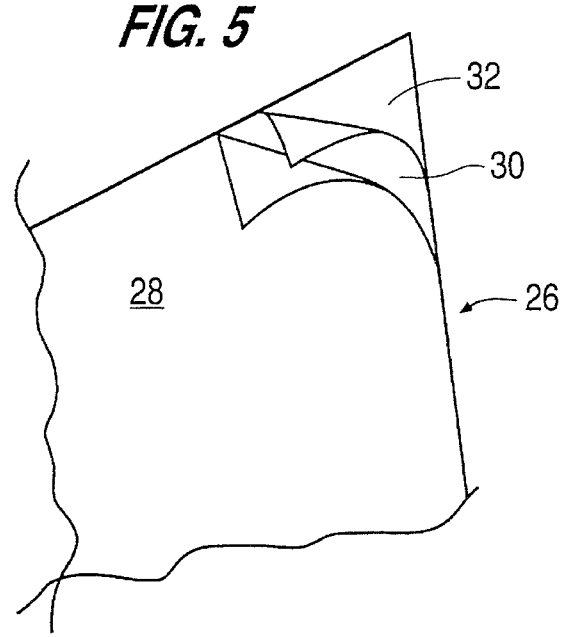
FIG. 5 is a perspective view showing a laminate structure of packaging material which could be used to make the pouches and roll of FIG. 4.

The packaging material is a multi-layer laminate 26, a three layer example of which is illustrated in FIG. 5. Laminate packaging material may have several layers of metal foils and plastic films laminated together in various configurations. A three layer laminate is shown and described for ease of explanation, however any variations in the number or order of layers of types of materials are contemplated to be within the scope of the invention. Laminates are known as strong, moisture-impervious packaging materials.

Figure 6:
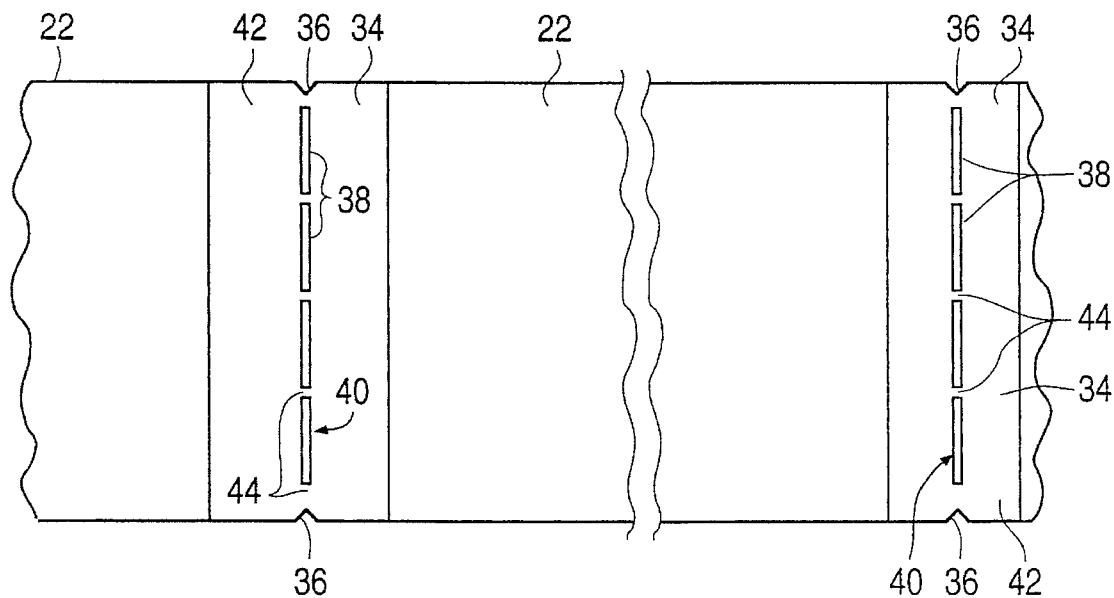
FIG. 6 is a schematic top plan view of a portion of the roll of FIG. 4.

In general, laminates are comprised of plastic films and metal foils laminated together, and plastic films are used as the innermost and outermost layers. For illustrative purposes, laminate 26 of FIG. 5 comprises an innermost layer 28 which may be a polyethylene film, middle layer 30 which is a metal foil, and outermost layer 32 which may be a polyester film. Innermost plastic film 28, metal foil 30 and outermost plastic film 32 laminated together form a very strong laminate packaging material which is impervious to moisture. Elongate pieces of laminate 26 are arranged one on top of another so that their innermost plastic films 28 face one another and are sealed together along their longitudinal sides. Pouches 22 are formed by sealing the laminates laterally, the innermost plastic films 28 being sealed together. Sealed areas 34 are thus provided between adjacent ones of pouches 22, as best seen in FIG. 6.

Laminate 26 is a high strength material which is generally tear resistant. Sealed areas 34 may be cut with scissors or the like to separate the pouches, but the present invention provides specially formed and located perforations to facilitate quick separation of the pouches without the need for cutting tools. When conventional punched perforations were provided in sealed area 34 and adjacent pouches torn apart, the moisture-impervious seal of each of the pouches was compromised. Plastic films like polyester and polyethylene tend to stretch instead of tearing, even when perforated, and do not tear straight. When uncontrolled tearing or stretching occurs, the seals of the pouches can be damaged resulting in air getting inside the pouches and exposing the bandaging article to atmospheric moisture. The presence of moisture inside the pouches will activate curing of the resin and thereby harden the bandaging article making it useless.

It has been found that providing a notch 36 on either side of sealed area 34, and providing linear perforations 38 extending laterally across the sealed area from notch to notch results in a readily tearable tear-line 40 in perforated portion 42. Because of the high strength of the laminate material and the resultant high strength of sealed area 34 that is formed, it has been found that only a small percentage of the laminates in sealed area 34 need to be connected to hold adjacent pouches 22 together. In order to ensure that the laminates tear instead of stretching apart, the combination of notches 36 and perforations 38 comprise between 55% to 95%, and preferably at least 80% of tear-line 40. In other words preferably at least 80% of tear-line 40 is characterized by the absence of material; or preferably at most 20% of tear-line 40 is comprised of connected portions 44. A relatively small portion of tear-line 40 is comprised of connected portions 44. In determining the proportion of connected portions to perforations and notches, the primary consideration is to leave just enough connected area to hold the pouches together.

The preferred shape of bandaging article 10 is rectangular and the preferred sizes are four-by-twelve inches or five-by-twenty-six inches. For both sizes, the preferred width of the laminate packaging material is seven-and-one-half inches. Using the same width of laminate for both sizes of articles is an economical consideration. Therefore, sealed areas 34 are seven and one-half inches across with notches and perforations appropriately sized to fall within the preferred ranges. Preferably four to five pouches will be connected together in a roll.

Of course, any desired shape or size of the article and number of pouches in a roll is within the scope of the present invention, and may depend on whether the medical bandaging article disclosed herein is used in splinting or casting to immobilize the injured body member. Either the foam layer or the fabric layer may be substantially larger than the other layers to provide extended portions for wrapping or securing around the body member.

When article 10 is to be applied to a patient, a pouch is torn off from the roll along the perforations and the bandaging article removed from its pouch. For best results, the bandaging article is wetted in water then laid on a towel or other working surface and smoothed flat. The foam side of the bandaging article is then applied against the skin of the patient and the article is shaped, molded and formed as necessary to support the injured body member. Within approximately four minutes the bandaging article hardens so that molding can no longer be done. The bandaging article becomes "set" approximately five to eight minutes from wetting, and becomes functional for supporting the injured body member in approximately twenty minutes. Total curing of the resin may take up to twenty four hours.

It will be evident that there are a number of changes, adaptations, and modifications of the present invention which come within the province of those skilled in the art. However, it is intended that all such variations not departing from the spirit of the invention be considered as within the scope thereof as limited only by the claims appended hereto.

I claim:

1. A medical bandaging article comprising:

a soft, resilient open cell foam padding layer;

a soft, flexible, water permeable fabric layer;

a flexible substrate smaller than said foam layer and said fabric layer, said substrate disposed between said foam layer and said fabric layer and impregnated or coated with a soft curable resin which hardens upon exposure to moisture to form a rigid structure; and a heat fusing web interposed between said fabric layer and said foam layer along at least one side of said substrate, said web providing a resin seepage barrier;

wherein upon application of heat and pressure sufficient to activate said web, said foam layer and said fabric layer are fused together on at least said one side of said substrate said web providing a resin seepage barrier and encasing said substrate to maintain all components of said article in proper position.

2. The medical bandaging article of claim 1, wherein said fusing web extends around the periphery of said substrate such that upon application of heat and pressure sufficient to activate said fusing web, said foam layer and said fabric layer are fused together around the periphery of said substrate to thereby encase said substrate.

3. The medical bandaging; article of claim 1, wherein said substrate is knit of fiberglass fibers with a mesh size of approximately 40 openings per square inch.

4. The medical bandaging article of claim 1, wherein at least six layers of said substrate are provided to provide sufficient rigidity to the article.

5. The medical bandaging article of claim 5, wherein said foam layer, said fabric layer and said fusing web are substantially equal in size, and said substrate is smaller to provide a fusing area around the periphery of said substrate.

6. The medical bandaging article of claim 6, wherein said foam layer, said fabric layer and said fusing web are larger than said substrate so as to provide at least a one-half inch allowance for said fusing area around the periphery of said substrate.

7. The medical bandaging article of claim 1, further comprising a second heat fusing web interposed between said foam layer and said substrate and extending around the periphery of said substrate for facilitating fusing around the periphery of said substrate upon application of sufficient heat and pressure.

8. The medical bandaging article of claim 1, wherein said fabric layer comprises a woven fabric.

9. The medical bandaging article of claim 8, wherein said woven fabric is flannel.

10. A medical bandaging article comprising:

a soft, resilient open cell foam padding layer:

a soft, flexible fabric layer:

a flexible substrate smaller than said foam layer and said fabric layer, said substrate disposed between said foam layer and said fabric layer and impregnated or coated with a soft curable resin which hardens upon exposure to moisture to form a rigid structure; and a heat fusing web interposed between said fabric layer and said foam layer, said web sized to extend around the periphery of and overlay said substrate to provide a barrier between said fabric layer and said substrate to prevent seepage of the resin through said fabric layer;

wherein upon application of heat and pressure sufficient to activate said web said foam layer and said fabric layer are fused together encasing said substrate to maintain all components of said article in proper position.

11. A medical bandaging article comprising:

a soft, resilient open cell foam padding layer:

a soft, flexible fabric layer:

a flexible substrate smaller than said foam layer and said fabric layer, said substrate disposed between said foam layer and said fabric layer and impregnated or coated with a soft curable resin which hardens upon exposure to moisture to form a rigid structure:

first heat fusing web interposed between said fabric layer and said substrate providing a barrier to prevent seepage of the resin through said fabric layer:

a second heat fusing web interposed between said foam layer and said substrate wherein said second fusing web is sized to extend around and overlay said substrate to provide a barrier between said foam layer and said substrate to prevent seepage of the resin through said foam layer; and wherein upon application of heat and pressure sufficient to activate said first and second webs said foam layer and said fabric layer are fused together encasing said substrate to maintain all components of said article in proper position.

12. A moisture-impervious packaging system for retaining a plurality of individually sealed medical bandaging articles in a moisture-free condition until use, each of said medical bandaging articles having a soft, resilient open cell foam padding layer, a soft, flexible, water permeable fabric layer, a flexible substrate smaller than said foam layer and said fabric layer, said substrate disposed between said foam layer and said fabric layer and impregnated or coated with a soft curable resin which hardens upon exposure to moisture to form a rigid, self supporting structure, and a heat fusing web interposed between said fabric layer and said foam layer along at least one side of said substrate providing a resin seepage barrier, wherein upon application of heat and ;pressure sufficient to activate said web, said foam layer and said fabric layer are fused together on at least said one side of said substrate encasing said substrate to maintain all components of said article in proper position, said packaging system comprising:

a plurality of medical bandaging articles contained within individually sealed moisture-impervious pouches defining sealed areas therebetween, said pouches being arranged serially in a continuous roll; and a perforated portion formed in each of said sealed areas, each said portion comprising linear perforations extending laterally across said sealed area between said pouches for enabling separation of said pouches while maintaining the integrity of their seals, and notches formed at opposite lateral sides of said sealed area for facilitating separation.

13. The moisture-impervious packaging system of claim 12, wherein said notches and said perforations in each said perforated portion comprise at least 80% of said sealed area.

14. A combination of a plurality of medical bandaging articles and a packaging system for containing individual ones of said articles in a moisture-free condition, said combination comprising:

a plurality medical bandaging articles each having a soft, resilient open cell foam padding layer, a soft, flexible, water permeable fabric layer, a flexible substrate smaller than said foam layer and said fabric layer, said substrate disposed between said foam layer and said fabric layer and impregnated or coated with a soft curable resin which hardens upon exposure to moisture to form a rigid, self supporting structure, and a heat fusing web interposed between said fabric layer and said foam layer along at least one side of said substrate providing a resin seepage barrier, wherein upon application of heat and pressure sufficient to activate said, said foam layer and said fabric layer are fused together on at least said one side of said substrate encasing said substrate to maintain all components of said article in proper position; and a packaging system having a plurality of medical bandaging articles contained within individually sealed moisture-impervious pouches defining sealed areas therebetween, said pouches being arranged serially in a continuous roll, and a perforated portion formed in each of said sealed areas, each said portion comprising linear perforations extending laterally across said sealed area between said pouches for enabling separation of said pouches while maintaining the integrity of their seals, and notches formed at opposite lateral sides of said sealed area for facilitating separation.

* * * * *